(12) United States Patent
Kim et al.

(10) Patent No.: US 8,044,663 B2
(45) Date of Patent: Oct. 25, 2011

(54) ULTRA-SENSITIVE SUSCEPTIBILITY DETECTION APPARATUS OF ANHARMONIC RESONANCE MEASUREMENT TYPE USING ATOMIC MAGNETOMETER, AND METHOD OF USING SAME

(75) Inventors: Ki Woong Kim, Daejeon (KR); Yong Ho Lee, Daejeon (KR); Hyuk Chan Kwon, Daejeon (KR); Jin Mok Kim, Daejeon (KR); Yong Ki Park, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 355 days.

(21) Appl. No.: 12/266,726

(22) Filed: Nov. 7, 2008

(65) Prior Publication Data

US 2010/0327869 A1 Dec. 30, 2010

(30) Foreign Application Priority Data

Jun. 11, 2008 (KR) ........................ 10-2008-0054638

(51) Int. Cl.
*G01V 3/00* (2006.01)
(52) U.S. Cl. ..................................................... 324/309
(58) Field of Classification Search ........... 324/300–322
See application file for complete search history.

(56) References Cited

U.S. PATENT DOCUMENTS 6,477,398 B1 * 11/2002 Mills ............................ 600/409
6,919,770 B2 * 7/2005 Happer et al. ............... 331/94.1

OTHER PUBLICATIONS

M. K., et al., *Maintenance and Improvement of Electromagnetic Metrology*, pp. 193-194, Dec. 31, 2005.

* cited by examiner

*Primary Examiner* — Dixomara Vargas
(74) *Attorney, Agent, or Firm* — Allen, Dyer, Doppelt, Milbrath & Gilchrist, P.A.

(57) ABSTRACT

The ultra-sensitive susceptibility detection apparatus of anharmonic resonance measurement type using an atomic magnetometer detects a change in susceptibility by a specimen containing an object to be measured. The apparatus includes an atomic magnetometer. The atomic magnetometer includes a cell containing an alkaline metallic atom, a light source for magnetically polarizing the alkaline metallic atom of the cell, and a bias magnetic field applicator for applying a bias magnetic field to adjust a measuring resonance frequency of the alkaline metallic atom. The apparatus includes an excitation magnetic field applicator for applying an excitation magnetic fields of different frequencies to magnetically excite the specimen, but not to couple the excitation field directly to the measuring atomic resonance frequency, and a measuring device for measuring a change in magnetic polarization of the alkaline metallic atom, which is affected by a magnetic field caused by the specimen being magnetically excited by the excitation magnetic field.

20 Claims, 7 Drawing Sheets

ULTRA-SENSITIVE SUSCEPTIBILITY DETECTION APPARATUS OF ANHARMONIC RESONANCE MEASUREMENT TYPE USING ATOMIC MAGNETOMETER, AND METHOD OF USING SAME

FIELD OF THE INVENTION

The present invention relates to an ultra-sensitive susceptibility detection apparatus of anharmonic resonance measurement type using an atomic magnetometer. More specifically, the invention relates to an ultra-sensitive susceptibility detection apparatus of anharmonic resonance measurement type using an atomic magnetometer and a method of using thereof, in which the high sensitivity of magnetic field measurement of an optical pumping atomic magnetometer is utilized to measure a change in AC magnetic susceptibility by a specimen to be measured, thereby enabling to detect an extremely small quantity of specimen (for example, bio-molecules attached to magnetic nanoparticles).

BACKGROUND OF THE INVENTION

In recent years, as research on genes and proteins has been extensively made, speedy and precision detection of bio-molecules such as protein, bacteria, virus, germ and DNA is required. Detection of bio-molecules employs mainly an antigen-antibody reaction method. Markers for particular pathogens such as cancer markers or cardiac markers are already commercialized in the form of a kit and extensively used in clinical and pathological examinations and the like.

Among the above techniques, the enzyme-linked immunosorbent assay (ELISA) method is explained hereafter. FIGS. 1a to 1c are diagrams illustrating a conventional enzyme-linked immunosorbent assay method. As shown in FIG. 1, in order to detect a particular antibody 12, a conjugated antigen 13 is disposed on a chip 10. The antibody 12 is combined to the conjugated antigen 13 arranged on the chip 10 by means of an antigen-antibody reaction. A fluorescent or isotopic marker 15 is combined to this antibody 12, which is then cleansed. Then, as illustrated in FIG. 1c, the antibody 12 after cleansing is combined with the antigen 13 and simultaneously with the marker 15. Thereafter, the intensity of fluorescence generated by the maker 15 is measured to detect the antibody 12 to be measured. In this enzyme-linked immunosorbent assay method, a combination procedure of the maker 14 is to be added, along with the cleansing and antigen-antibody reaction procedures, thereby resulting in a complicated process. In addition, the fluorescent material of the marker 15 is absorbed in the antibody 12, disadvantageously leading to a reduction in the measuring accuracy.

As a simplified and precision technique, relative to the enzyme-linked immunosorbent assay method, a susceptibility attenuation immuno-assay method has been developed. FIGS. 2a and 2b are schematic diagrams illustrating a convention susceptibility attenuation immuno-assay method using magnetic nanoparticles. As shown in FIG. 2a, this method employs a magnetic agent where an antigen 26 is attached to a magnetic nanoparticle 24 having a size of a bio-molecule. Here, the antigen 26 is a conjugated antigen which has a good affinity with the antibody 27 to be measured. Each of the respective magnetic nanoparticles 24 has a self magnetic moment and is enclosed with a layer 25 not to be agglomerated with each other. For example, the layer 25 is formed of Dextran.

As illustrated in FIG. 2b, if an external AC magnetic field is applied to the magnetic nanoparticles 24, the magnetic nanoparticles 24 spin in resonance with the external AC magnetic field. Here, the nanoparticles having different sizes spin in response to the AC magnetic fields having different frequencies. The magnetic nanoparticles, which spin in resonance, generate a magnetic field having the same frequency as the external AC magnetic field, thereby exhibiting a high susceptibility. If the magnetic nanoparticles 24 have a uniform size, the magnitude of oscillation in the magnetic moment exhibits a maximum peak at a particular frequency. Here, if an antibody 27 to be measured is contained in the magnetic agent solution, the magnetic nanoparticles 24, to which the antigen 26 is attached, is combined with each other by the antigen 27. The combined magnetic nanoparticles 30 cannot easily spin in response to a change in the external magnetic field, and consequently the antibody 27 in the magnetic agent reduces the AC susceptibility of the agent containing the magnetic nanoparticle 24. If the susceptibility where the antibody 27 is contained in the magnetic agent is normalized as being susceptibility when in absence of no antibody, a calibration curve can be obtained regardless of concentration of the magnetic agent and also a quantitative concentration of the antibody 27 can be determined.

That is, an AC magnetic field having a particular frequency and the change in the magnitude of magnetic field, which is generated by the magnetic nanoparticles 24 contained in the magnetic agent, is measured with precision, thereby enabling to detect the antibody 27 contained in the magnetic agent.

In this case, the detection device employs in generally an inductive detector using a coil. However, the inductive detector has a weak sensitivity to disadvantageously degrade the measuring sensitivity thereof. Thus, as a high sensitivity detector, a high-temperature superconducting quantum interference device (High-Tc SQUID) has been developed.

The above susceptibility attenuation immuno-assay method has advantages that the magnetic nanoparticle and the AC magnetic field are never reacted with an antibody to be measured, and the procedures are simplified. However, this method has a disadvantage that the measuring sensitivity totally relies on the detection device itself. In case of the above-mentioned inductive detector using a coil, a resonance circuit using a high Q value is required, but the resonance frequency of the induction coil cannot be easily changed.

The superconducting quantum interference device capable of more precision measurement has a high sensitivity, but since a superconducting phenomenon is employed, it consumes expensive coolant such as liquid helium. Thus, the maintenance cost thereof reaches about 20,000 to 80,000 dollars a year and the like. Accordingly, there is a demand to provide a new detection device not necessitating cooling.

SUMMARY OF THE INVENTION

Accordingly, the present invention has been made in view of the above-mentioned problems occurring in the prior art, and it is a primary object of the present invention to provide an ultra-sensitive susceptibility detection apparatus, which can be applied to a susceptibility attenuation immuno-assay method to thereby dramatically improve the sensitivity of the immuno-assay method.

Another object of the invention is to provide an ultra-sensitive susceptibility detection apparatus, which does not necessitate an expensive coolant and enables an easy measurement using an atomic magnetometer where the measuring resonance frequency can be easily shifted.

To accomplish the above object of the present invention, according to one aspect of the present invention, there is provided an ultra-sensitive susceptibility detection apparatus of anharmonic resonance measurement type using an atomic magnetometer, in which a change in susceptibility by a specimen containing an object to be measured is detected. The apparatus comprises an atomic magnetometer including: a cell containing an alkaline metallic atom, which is affected by a magnetic field caused by the specimen; a light source for magnetically polarizing the alkaline metallic atom of the cell; and a bias magnetic field applicator for applying a bias magnetic field Bo to adjust a measuring resonance frequency of the alkaline metallic atom. The apparatus further includes an excitation magnetic field applicator for applying an excitation magnetic field Bs to the specimen to magnetically excite the specimen, the AC excitation magnetic field Bs being comprised of a plurality of AC magnetic fields $Bs_1$ and $Bs_2$ having desired frequencies; and a measuring device for measuring a change in magnetic polarization of the alkaline metallic atom, which is affected by a magnetic field B caused by the specimen being magnetically excited by the excitation magnetic field Bs.

In an embodiment, the direction of the bias magnetic field Bo is in parallel to the direction of magnetic polarization of the alkaline metallic atom. In an embodiment, the AC excitation magnetic field Bs is perpendicular to the bias magnetic field Bo.

In an embodiment, the excitation magnetic field applicator is provided with a plurality of excitation coils for generating AC magnetic fields having desired frequencies, wherein the frequencies $f_1$ and $f_2$ of the respective AC magnetic fields and the integer times thereof have a value different from the measuring resonance frequency of the alkaline metallic atoms to prevent a direct effect on the atoms.

In an embodiment, the excitation magnetic field applicator further comprises a planar attenuation coil such that the excitation magnetic field Bs does not affect the cell.

In an embodiment, a linear summation $af_1+af_2$ of the frequencies $f_1$ and $f_2$ of the AC magnetic fields is the measuring resonance frequency $\gamma Bo/2\pi$ of the alkaline metallic atoms. In an embodiment, the cell is disposed inside an oven structure for shielding heat loss of the cell.

In an embodiment, the apparatus further comprises vacuum tubes around the cell to prevent a refraction index activity change in the heated air flow and to block heat loss from the cell.

In an embodiment, the measuring device includes: a polarized light source that radiates a linearly polarized light to the cell; and a transmitted light measurement and susceptibility detection portion for measuring a polarization angle of a transmitted light passing through the cell and for detecting susceptibility of the specimen based on a signal of the polarization angle. In an embodiment, the bias magnetic field applicator is formed of a plurality of coils capable of generating a uniform magnetic field. In an embodiment, the plurality of coils are Helmholtz coils.

In an embodiment, the apparatus further comprises a magnetic field shielding device for blocking magnetic field noise except for magnetic fields required for measurement.

In an embodiment, the object to be measured is bio-molecules treated with magnetic nanoparticles or other magnetic materials.

According to another aspect of the invention, there is a method of using an ultra-sensitive susceptibility detection apparatus of anharmonic resonance measurement type using an atomic magnetometer. The method comprises the steps of: filling a specimen in a specimen unit, the specimen containing an object to be measured; radiating light to a cell containing alkaline metallic atoms to optically pump the alkaline metallic atoms contained in the cell; applying a bias magnetic field Bo to the cell containing the optically pumped alkaline metallic atoms; applying an excitation magnetic field to the specimen unit, the excitation magnetic field including a plurality of AC magnetic fields $Bs_1$ and $Bs_2$ having desired frequencies $f_1$ and $f_2$ to excite the specimen; and detecting a change in susceptibility of the specimen, based on a change in magnetic polarization of the cell that is caused by a magnetic field B of the excited specimen through the excitation magnetic filed Bs.

In an embodiment, the light is a circular polarized light in the step of optically pumping.

In an embodiment, between the step of applying an excitation magnetic field and the step of detecting, the method further comprises the step of adjusting the bias magnetic field Bo such that a linear summation $af_1+af_2$ of the frequencies $f_1$ and $f_2$ of the plurality of the AC magnetic fields matches the measuring resonance frequency $\gamma Bo/2\pi$ of the atomic magnetometer.

In an embodiment, the step of applying the excitation magnetic field further comprises the step of attenuating the excitation magnetic field affecting the cell using a planar attenuation coil.

In an embodiment, the step of detecting includes the steps of: radiating a linearly polarized light to the cell; measuring a polarization angle of transmitted light passing through the cell; and detecting a change in the magnetic polarization of the alkaline metallic atoms, based on a signal of the polarization angle and detecting a change in susceptibility of the specimen.

In an embodiment, the method further comprises the step of obtaining concentration of bio-molecules based on the change in the susceptibility of the specimen.

In an embodiment, the step of obtaining the concentration of the bio-molecules includes the steps of: normalizing the change in the specimen susceptibility obtained in the step of detecting to a susceptibility of the specimen where the specimen does not contain bio-molecules to thereby obtain a calibration curve, and obtaining a quantitative concentration of the bio-molecules.

In some application such as detection of Malachite green molecules, the ultra-sensitivity susceptibility detection apparatus of enharmonic resonance measurement type using an atomic magnetometer is about ten million times sensitive as compared with the conventional inductive detector using coils, and a hundred times sensitive as compared with a system based on the conventional high temperature superconducting quantum interference device.

Further, in the ultra-sensitivity susceptibility detection apparatus of anharmonic resonance measurement type using an atomic magnetometer, a low temperature cooling is not required and thus an expensive coolant such as liquid helium is not necessary, thereby resulting in a reduced maintenance cost and easy maintenance.

In addition, the measuring resonance frequency can be easily varied. Therefore, the apparatus of the invention can be easily applied to the susceptibility attenuation immuno-assay method.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Hereinafter, preferred embodiments of the present invention will be described in detail with reference to the appended drawings. In the explanation of embodiments, details well-known in the art and not related directly to the invention may be omitted to avoid unnecessarily obscuring the invention and convey the gist of the invention more clearly.

Figure 1A:
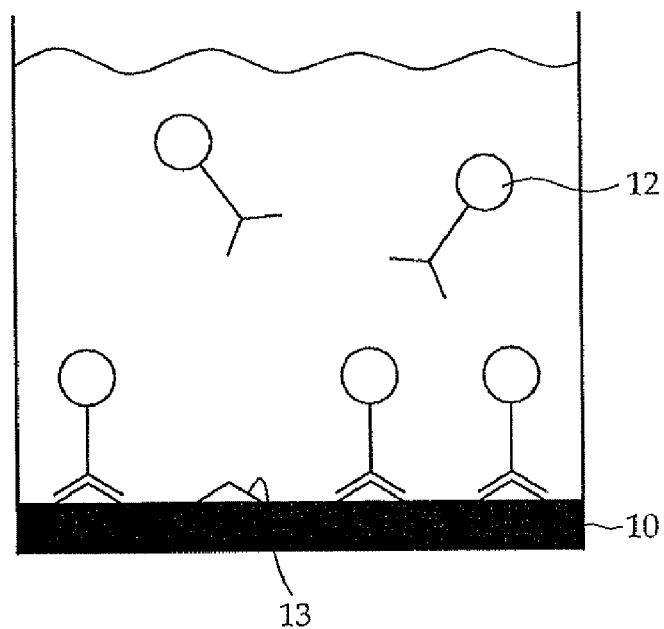
FIGS. 1a to 1c are diagrams illustrating a conventional enzyme-linked immunosorbent assay method.
Figure 1B:
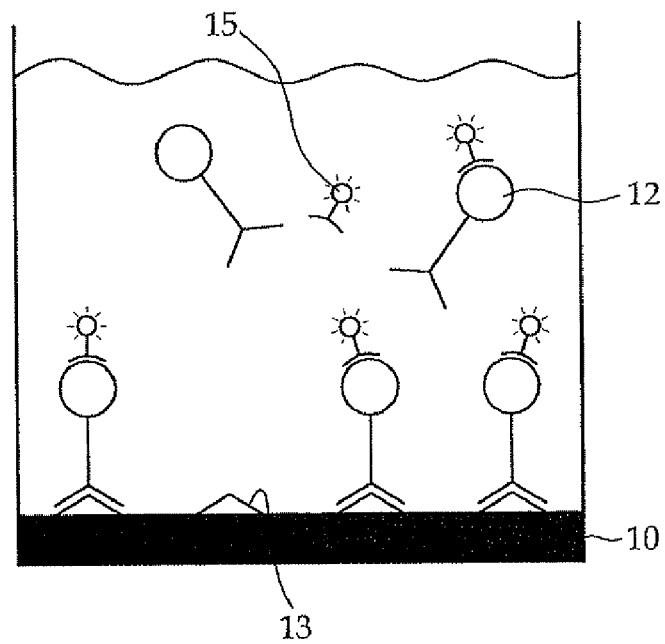
Figure 1C:
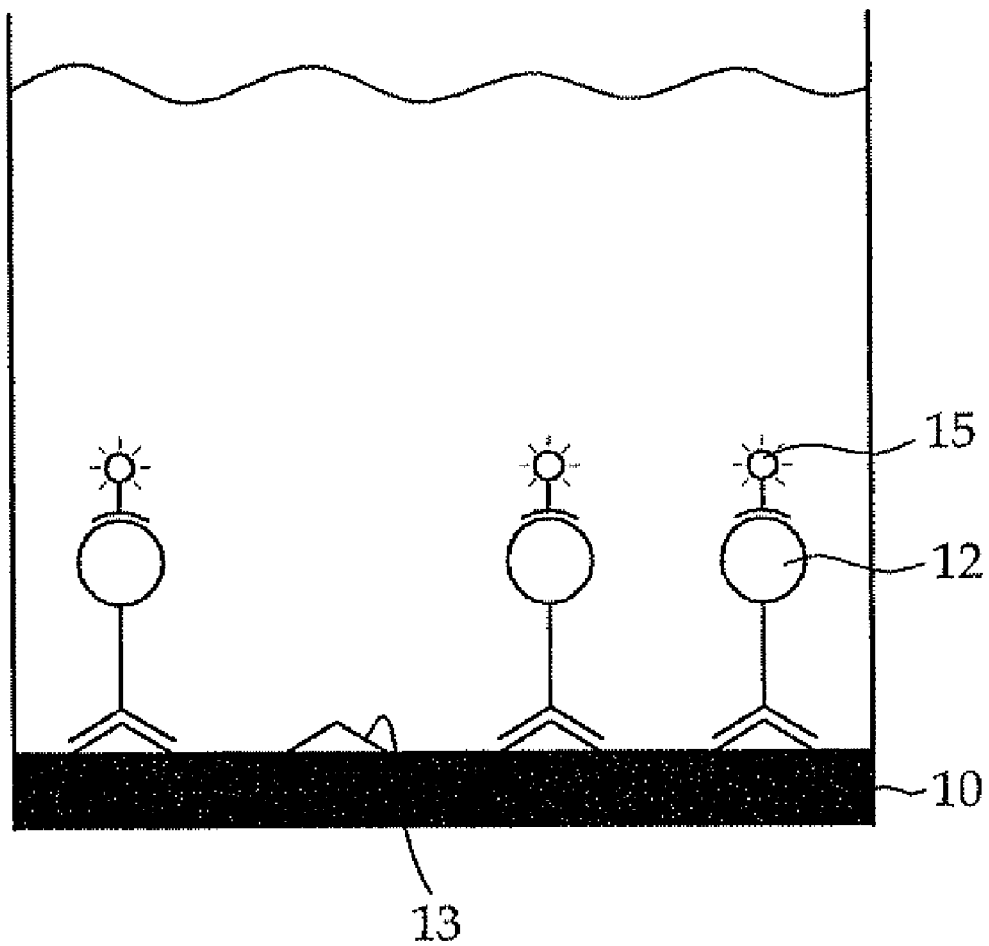
Figure 2A:
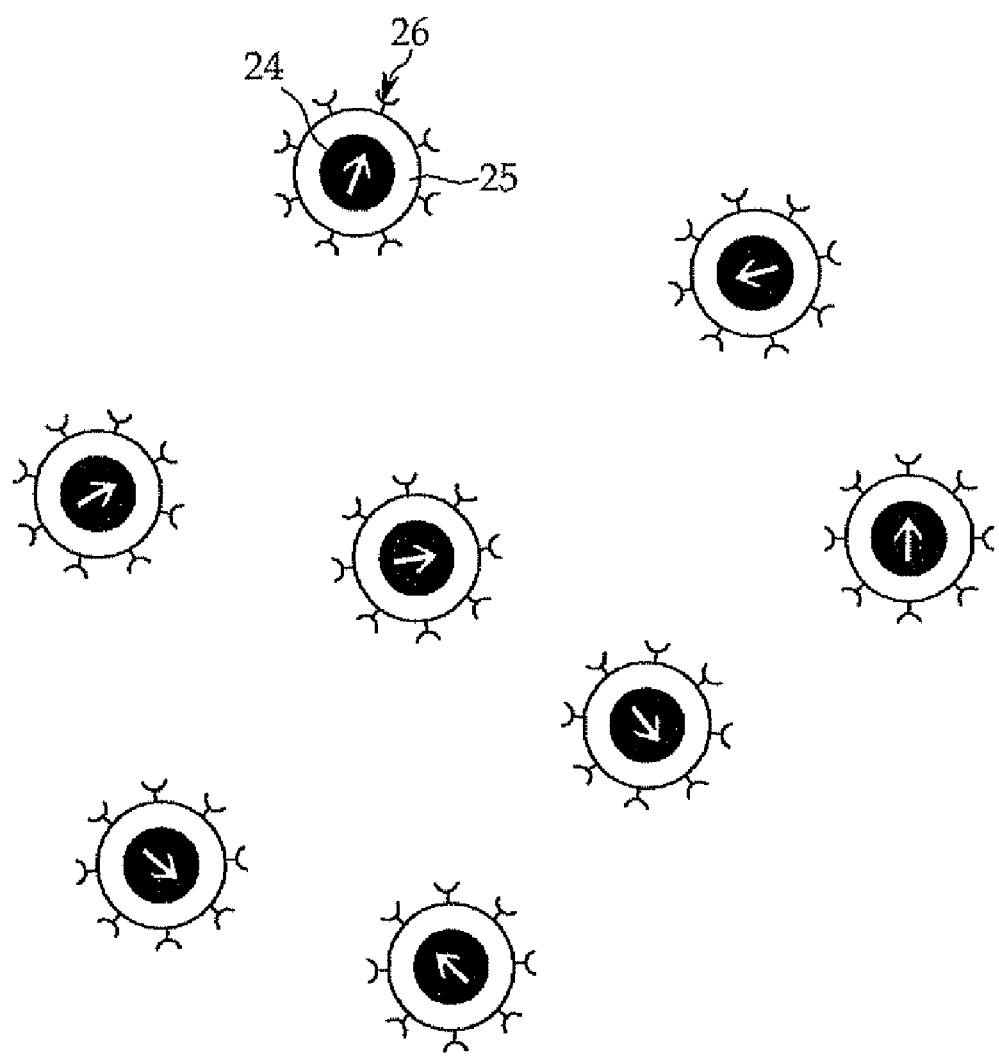
FIGS. 2a and 2b are schematic diagrams illustrating a convention susceptibility attenuation immuno-assay method using magnetic nanoparticles.
Figure 2B:
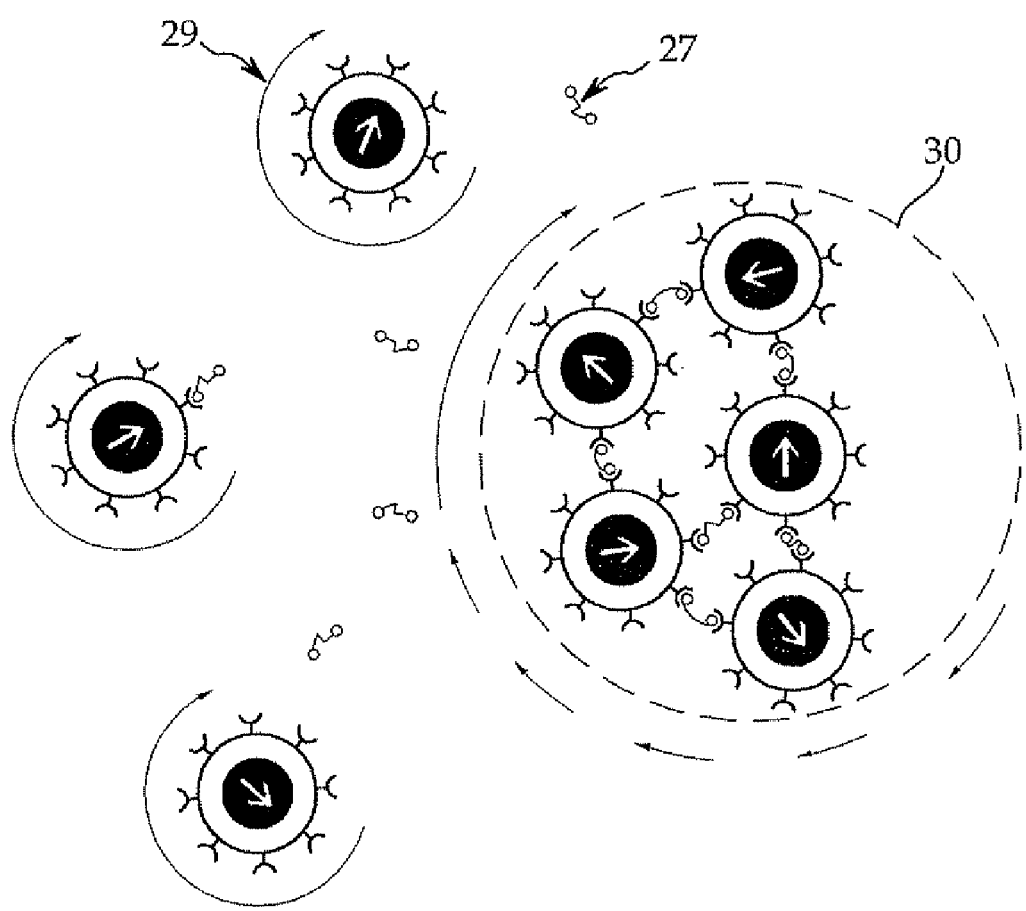
Figure 3:
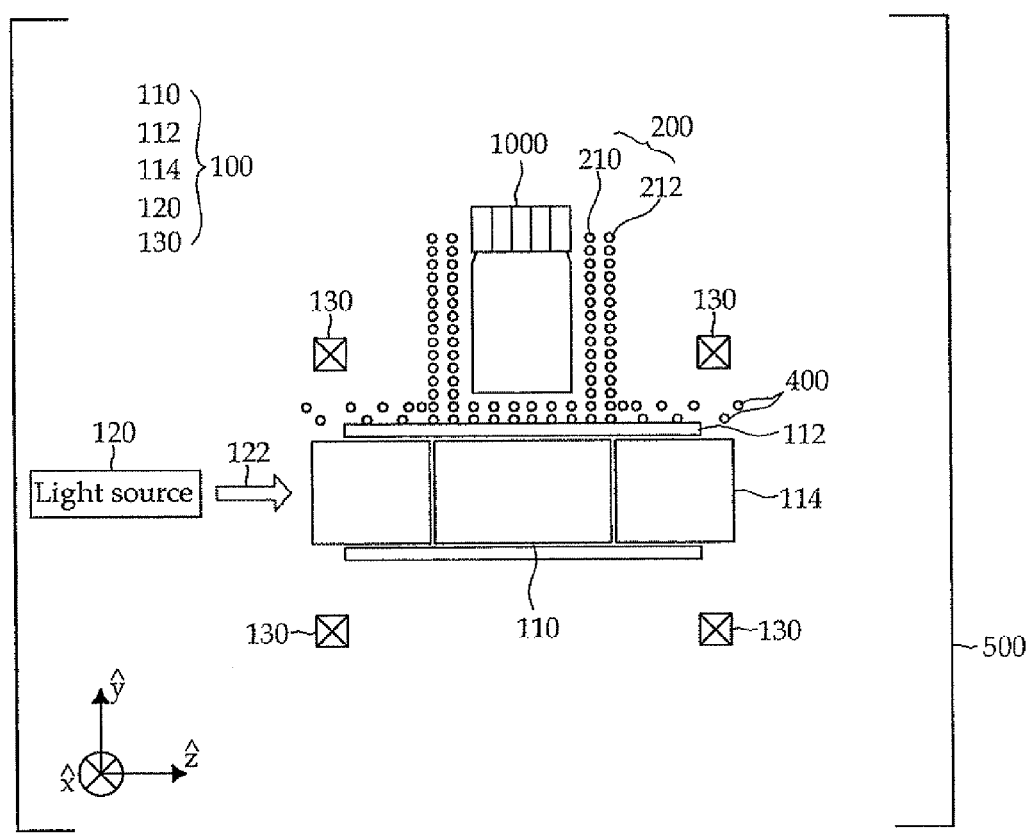
FIG. 3 is a vertical cross-section illustrating an atomic magnetometer for detecting susceptibility with ultra-sensitivity using anharmonic resonance measurement.
Figure 4:
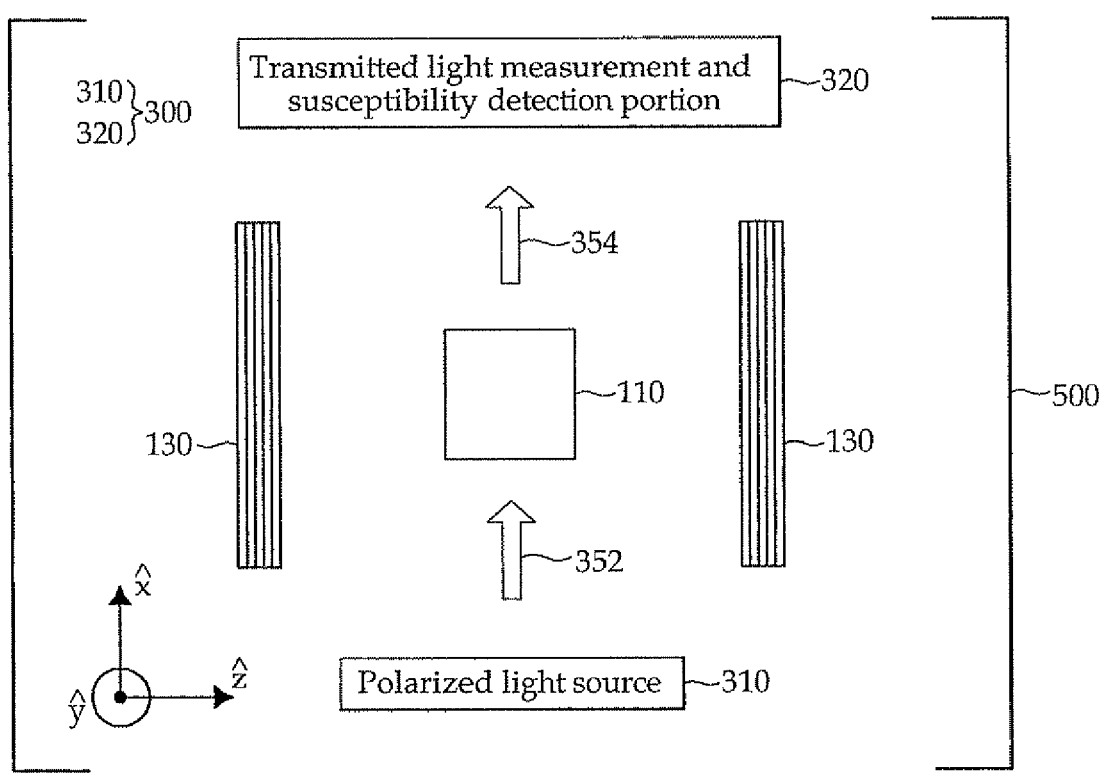
FIG. 4 is a transversal plan view of the apparatus of FIG. 3 seen from the y-axis.

Ultra-Sensitive Susceptibility Detection Apparatus of Anharmonic Resonance Measurement Type Using Atomic Magnetometer FIG. 3 is a vertical cross-section illustrating an ultra-sensitive susceptibility detection apparatus of anharmonic resonance measurement type using an atomic magnetometer according to an embodiment of the invention. FIG. 4 is a transversal plan view of the detection apparatus of FIG. 3 seen from the top thereof. Hereinafter, the ultra-sensitive susceptibility detection apparatus of anharmonic resonance measurement type using an atomic magnetometer atomic magnetometer is referred to as an "ultra-sensitivity susceptibility detection apparatus" for the purpose of convenient description.

The ultra-sensitivity susceptibility detection apparatus includes an atomic magnetometer 100, an excitation magnetic field applicator 200, a measuring device 300 and the like.

The atomic magnetometer 100 includes a cell 110 containing alkaline metallic atoms, a light source 120 for magnetic-polarizing the alkaline metallic atoms, a bias magnetic field applicator 130 for controlling magnetic resonance frequency of the alkaline metallic atoms, and the like.

The cell 110 contains the alkaline metallic atoms and buffer gases. The alkaline metallic atom includes potassium, rubidium, cesium and the like. The buffer gas employs an inert gas such as helium, xenon, and the like. Further, nitrogen gas can be used as a quenching gas.

The cell 110 is disposed inside an oven structure 112. A vacuum tube 114 is disposed between the cell 110 and the light source 120, which will be further described hereinafter. The oven structure 112 serves to shield heat loss to the outside from the cell 110 containing alkaline metallic atoms. The oven structure 112 controls vapor pressure of the alkaline metallic atoms through electric heating, circulation of hot air, circulation of hot water, or the like.

Provided around the cell 110 is the vacuum tube 114. The vacuum tube 114 acts as a window of the oven structure 112 for shielding heat loss of the cell 110. In addition, the vacuum tube 114 is formed of vacuum using a material such as glass, and prevents a change in the refractivity of the heated air through the light path.

The light source 120 outputs a desired light 122 to the cell 110 to optically pump the alkaline metallic atoms contained in the cell 110. Here, the light 122 output from the light source 120 may be a circular polarized light. When a desired light is irradiated by the light source 120, the alkaline metallic atom vapor inside the cell 110 absorbs the circular polarized light having a particular frequency according to the quantum mechanical selection rule. The alkaline metallic atoms become a single quantum state by means of repeated absorption and discharging. That is, an optical pumping is carried out. The optically pumped alkaline metallic atoms spin in one direction, and a magnetic polarization (magnetization) occurs in parallel to the direction. The direction of the magnetic polarization will be the z-axis in FIG. 3.

The bias magnetic field applicator 130 applies a desired bias magnetic field Bo to the cell 110. The direction of the bias magnetic field Bo is in parallel to the direction of the magnetic polarization of the alkaline metallic atoms. The bias magnetic field applicator 130 is comprised of a plurality of coils to enable to form a uniform magnetic field. For example, Helmholtz coil may be employed. The Helmholtz coil provides a uniform magnetic field in a large space and thus is suitable for the present invention. The alkaline metallic atoms perform a precession motion about the axis, to which the bias magnetic field Bo is applied, by means of the bias magnetic field Bo. Here, the angular velocity of the precession motion is γBo, in which γ is the gyromagnetic ratio of the alkaline metallic atom.

A specimen to be measured is placed in a specimen unit 1000. The specimen unit 1000 is placed above the atomic magnetometer 100. The specimen unit 1000 is heat-shielded by the oven structure 112. The specimen contains an object to be measured as to a change in the susceptibility (hereinafter, referred to as a "measured object"). The measured object includes bacterial, virus, DNA and the like, and any others as long as they are to be measured as to a change in the susceptibility thereof. In particular, if the measured object is an antibody in a bio-molecule, the specimen is a mixture of an antibody and magnetic nanoparticles to which an antigen is attached. That is, it is the state of a bio-molecule treated with magnetic nanoparticles.

The excitation magnetic field applicator 200 applies an excitation magnetic field Bs to the specimen contained in the specimen unit 100, in particular the magnetic nanoparticles contained therein. The direction of the excitation magnetic field Bs is perpendicular to that of the bias magnetic field Bo. The excitation magnetic field applicator 200 is formed of a plurality of excitation coils 210 and 212 in order to utilize a enharmonic modulation method. The respective excitation coils 210 and 212 generate AC magnetic fields $Bs_1$ and $Bs_2$ having desired frequencies $f_1$ and $f_2$. The plural AC magnetic fields $Bs_1$ and $Bs_2$, which are generated from the plural excitation coils 210 and 212, respectively, are the excitation magnetic field Bs.

In case where a single excitation coil 210 is used to apply an excitation magnetic field Bs directly to the specimen and thus magnetically excite the specimen, the excitation magnetic field Bs is stronger than that caused by the specimen. Therefore, the alkaline metallic atoms contained the cell 110 is first reacted with the excitation magnetic field Bs, thereby being unable to measure the susceptibility of the specimen to be measured. Thus, an anharmonic modulation technique is utilized to prevent the cell 110 from responding directly to the excitation magnetic field Bs.

Hereafter, the excitation magnetic field applicator 220 using an anharmonic modulation method will be explained in detail. For the purpose of convenient explanation, the excitation magnetic field applicator 200 will be illustrated as having two excitation coils 210 and 212. One of the two excitation coils is denoted by a first excitation coil 210, and the other one by a second excitation coil 212. However, the number of the excitation coils 210 and 212 are not limited to the above two excitation coils.

The first excitation coil 210 applies an AC magnetic field $Bs_1$ having a desired first frequency $f_1$ to the specimen unit 1000, and the second excitation coil 212 applies an AC magnetic field $Bs_2$ having a desired second frequency $f_2$ to the specimen unit 1000. Here, the first frequency $f_1$ and the second frequency $f_2$, and the integer times thereof are to have a value different from the measuring resonance frequency $\gamma Bo/2\pi$ of the alkaline metallic atoms. Here, the first and second frequencies $f_1$ and $f_2$ of the applied AC magnetic fields $Bs_1$ and $Bs_2$ are on the order of several kHz, and the reaction linewidth (i.e., magnetic resonance linewidth) of the atomic magnetometer 100 is on the order of about 100 Hz. Thus, when the first and second excitation coils 210 and 212 apply a plurality of AC magnetic fields $Bs_1$ and $Bs_2$, i.e., the excitation magnetic field Bs, the cell 110 cannot be directly affected.

In case where a single excitation coil 210 applies an AC magnetic field Bs1 to the specimen, the magnitude of magnetic polarization of the specimen is expressed by the following mathematical equation 1. The mathematical equation 1 represents a case where the magnetic nanoparticle contained in the specimen is iron oxide particles of about 30 nm. Since the magnetization of the iron oxide particles is about 50 kA/m and the size ratio of magnetic energy at room temperature is very small on the order of $10^{-3}$, the magnitude of magnetic polarization (magnetization) can be expressed as follows.

$$M(\zeta \to 0) = 0.32H(\mu_o m/k_B T) - 0.12H^3 (\mu_o m/k_B T)^3 +$$

[Mathematical Equation 1]

Here, M denotes the total magnetization, $\mu_o$ denotes a vacuum susceptibility, m denotes the magnitude of magnetization of a single magnetic nanoparticle, H is an external magnetic field, $k_B$ is the Boltzmann constant, and T is a temperature.

The magnetic polarization of magnetic nanoparticles generates non-linear terms, which is proportional to high-order terms such as the third-order power of the external magnetic field. Therefore, if separate individual excitation coils 210 and 212 are used to apply AC magnetic fields $Bs_1$ and $Bs_2$ having desired frequencies $f_1$ and $f_2$, the magnetic nanoparticles are magnetically excited and generate a magnetic field B having a harmonic frequency due to the high-order non-linear terms. The harmonic frequency corresponds to $af_1+bf_2$. Consequently, the magnetic field B caused by the specimen has a frequency of $af_1+bf_2$, where a and b are arbitrary integers.

Hereafter, the measuring device 300 will be explained. The measuring device 300 detects susceptibility of the specimen in such a way to measure a change in the magnetic polarization of the alkaline metallic atoms, which are affected by the magnetic field B by the magnetically excited specimen. As illustrated in FIG. 4, the measuring device 300 includes a polarized light source 310, and a transmitted light measurement and susceptibility detection portion 320.

The polarized light source 310 radiates an incident light 352 to the cell 110 containing the alkaline metallic atoms, which are affected by the magnetic field B by the specimen. Here, it is preferable that the incident light 352 employs a linearly polarized light. In addition, preferably the linearly polarized light has a frequency slightly deviated from the optical absorption wavelength of the alkaline metallic atoms. As illustrated in FIG. 4, the linearly polarized light 352 is radiated in the x-axis direction. The polarization angle in the linearly polarized light 352 changes in proportion to the x-axis projection component of the magnetic polarization of the alkaline metallic atoms, which are contained in the cell 110.

The transmitted light measurement and susceptibility detection portion 320 at first measures light transmitted through the cell 110 and detects a change in the magnetic polarization of the alkaline metallic atoms. As shown in FIG. 4, the polarization angle of the transmitted light 354, which has passed through the cell 110, is in proportion to the x-axis projection component of the magnetic polarization of the alkaline metallic atoms. By using the transmitted light measurement and susceptibility detection portion 320, a signal having a frequency of $\gamma Bo/2\pi$ can be obtained from the transmitted light 354. The amplitude of the signal is in proportion to the amount of the magnetic nanoparticle that are not combined due to the antibody in the specimen unit 1000. In case where a larger amount of biomolecules (antibodies) that is the measured object, is contained in the specimen unit 1000, magnetic nanoparticles attached to the antibodies are combined with each other by means of the antigen-antibody reaction to form a magnetic nanoparticle group. This magnetic nanoparticle group has a larger moment of inertia. The magnetic nanoparticle group having the larger moment of inertia does not respond to an excitation magnetic field Bs corresponding to a particular spinning frequency of the respective magnetic nanoparticle. Therefore, as the specimen unit 1000 contains a lager amount of bio-molecules, the amount of magnetic nanoparticles that is not combined to each other through the bio-molecules becomes smaller. Thus, the amplitude of a signal obtained from the transmitted light 354 becomes smaller. This reduction in the signal amplitude denotes a reduction in the AC susceptibility of the specimen.

Based on the signal obtained from the transmitted light, the transmitted light measurement and susceptibility detection portion 320 then detects susceptibility of the specimen, from which the amount of bio-molecules contained in the specimen can be estimated. Further, the transmitted light measurement and susceptibility detection portion 320 normalizes susceptibility of the magnetic nanoparticles where bio-molecules are contained in the specimen unit 100 to obtain a calibration curve. Based on the calibration curve, the concentration of bio-molecules can be obtained in a quantitative manner.

In an embodiment, the ultra-sensitivity AC susceptibility detector may further comprise a magnetic field shielding device 500. A magnetic field affecting the cell 110 is to be restricted to the magnetic field B caused by the specimen. Thus, it may need a magnetic field shielding device 500 for blocking magnetic field noises, except for measuring conditions. The magnetic field shielding device 500 may be a passive magnetic field shielding device 500 formed of a soft magnetic material such as mu metals, or an active magnetic field shielding device 500 formed of a combination of coils.

In addition, preferably the excitation magnetic field applicator 200 may further comprise an attenuation coil 400. The attenuation coil 400 is connected in series with the excitation magnetic field applicator 200, i.e., with the excitation coils 210 and 212 respectively. Further, as illustrated in FIG. 3, the attenuation coil 400 is provided on the xz plane so as to be perpendicular to the excitation coils 210 and 212. The strong AC magnetic fields $Bs_1$ and $Bs_2$ caused by the excitation coils 210 and 212 broaden the linewidth of the atomic magnetometer 100 to thereby reduce the sensitivity of magnetic field. Thus, the attenuation coil 400 is provided in order for the AC magnetic field $Bs_1$ and $Bs_2$ by the excitation coils 210 and 220 not to affect the cell 110 as possible as can. It is preferable that a plurality of attenuation coils 400 is connected in series with the respective excitation coils 210 and 220.

Figure 5:
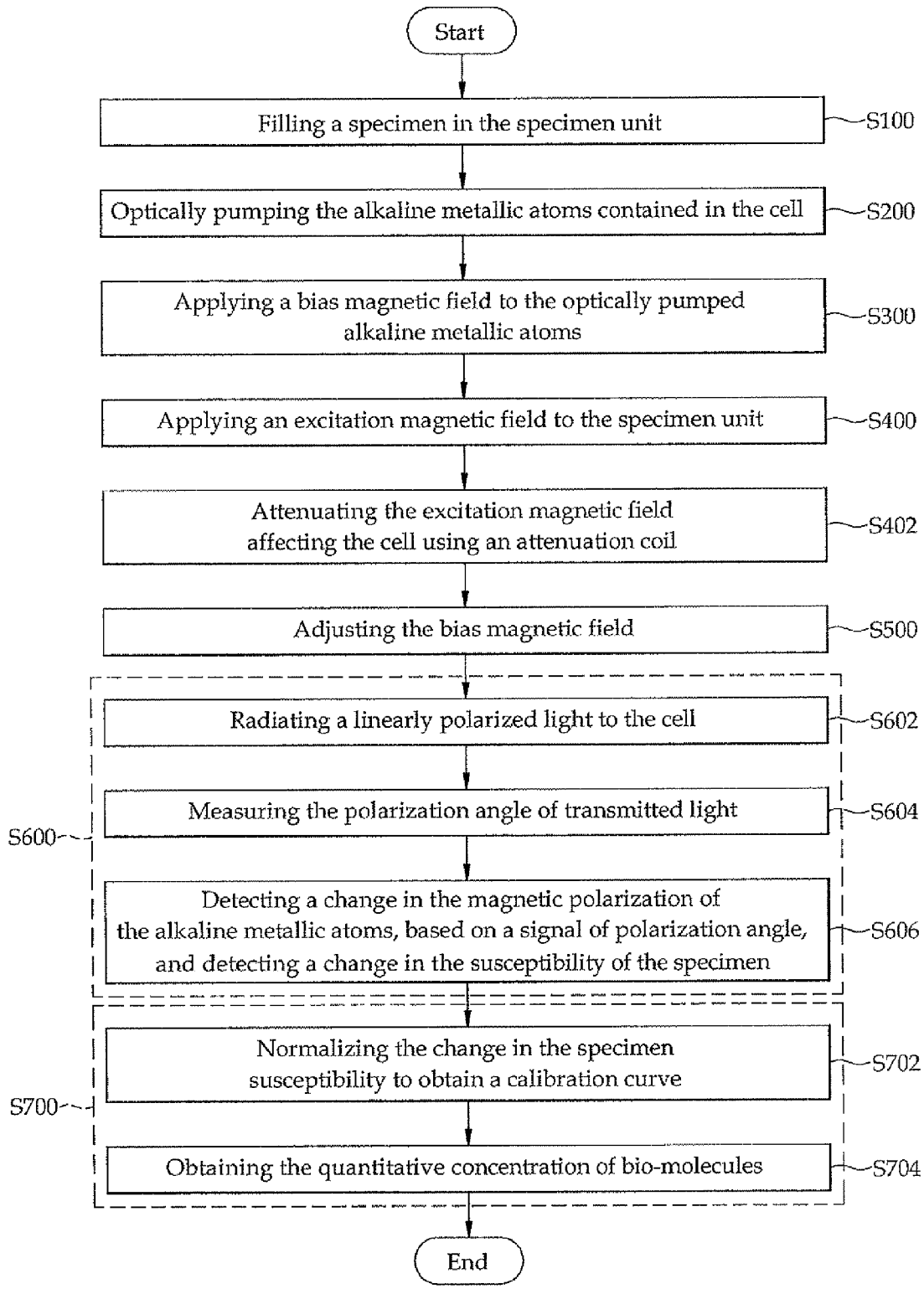
FIG. 5 is a flow diagram showing a method of using an ultra-sensitive AC susceptibility detection apparatus using an atomic magnetometer according to an embodiment of the invention.

Use of Ultra-Sensitive AC Susceptibility Measuring Apparatus Using Atomic Magnetometer FIG. 5 is a flow diagram showing a method of using an ultra-sensitivity susceptibility detection apparatus using an atomic magnetometer according to an embodiment of the invention.

First, a specimen containing an object to be measured (a measured object) is filled in the specimen unit 1000. As previously mentioned, the specimen contains bio-molecules treated with magnetic nanoparticles or a magnetic body.

The light source 120 radiates a desired light to the cell 110 to optically pump the alkaline metallic atoms contained in the cell 110 (S200). The alkaline metallic atoms come to have a quantum state through light absorption and emission. That is, the alkaline metallic atoms are made to spin in one direction, in parallel to which magnetic polarization occurs. The direction of the magnetic polarization will be the z-axis direction in the coordinate system of FIG. 3.

Thereafter, the bias magnetic field applicator 130 applies a bias magnetic field Bo to the cell 110 that contains the optically pumped alkaline metallic atoms (S300). Here, the applied bias magnetic field Bo has the same direction as that of magnetic polarization of the alkaline metallic atoms. The alkaline metallic atoms, to which the bias magnetic field Bo is applied, perform a precession motion with an angular velocity of γBo about the axis of the bias magnetic field Bo (the z-axis in FIG. 4).

Thereafter, an excitation magnetic field Bs is applied to the specimen unit 1000 (S400). In the application of excitation magnetic field (S400), it is preferable that a plurality of excitation coils 210 and 212 is used to apply AC magnetic fields $Bs_1$ and $Bs_2$ having desired frequencies $f_1$ and $f_2$ i.e., an anharmonic modulation method. In case where the magnetic nanoparticles contained in the specimen unit 1000 have a uniform size, the reaction of the magnetic nanoparticles (generation of a magnetic field B by the specimen) by the AC magnetic fields Bs1 and Bs2 having different frequencies is predominant at the linear combination $af_1 + bf_2$ of the respective frequencies.

The excitation coils 210 and 212 apply AC magnetic fields $Bs_1$ and $Bs_2$. Then, the specimen unit 1000, which has been magnetically excited by the excitation magnetic field Bs, generates a magnetic field B having a frequency corresponding to $af_1 + af_2$ (S500). This magnetic field B caused by the specimen affects the alkaline metallic atoms contained in the cell 110. Due to the nuclear magnetic resonance theory, magnetic polarization of the alkaline metallic atoms lies on the xy plane in the coordinate system in FIG. 4, to thereby create an x-axis component of the magnetic polarization. The x-axis component of magnetic polarization oscillates with a frequency of γBo/2π due to precession motion. The x-axis component of magnetic polarization of the alkaline metallic atoms occurs only when the magnetic field B caused by the specimen and oscillating with a frequency of γBo/2π is applied to the cell 110.

Thus, before the detection step S600, which will be described hereafter, it is preferable that the frequency $af_1 + bf_2$ of the magnetic field B by the specimen is modulated into γBo/2π (S500). The frequency modulation may be performed through adjustment of the respective frequencies $f_1$ and $f_2$ such that the linear combination $af_1 + bf_2$ of the frequencies of the AC magnetic fields $Bs_1$ and $Bs_2$, which are generated from plural excitation coils 210 and 212, becomes γBo/2π. In addition, the bias magnetic field Bo may be controlled to modulate the frequencies. If the bias magnetic field Bo is adjusted to shift the measuring resonance frequency γBo/2π of the atomic magnetometer 100, the magnetic field B caused by the specimen only can be used to induce reaction of the alkaline metallic atoms.

Further, in the step of excitation magnetic field (S400), it is preferable that an attenuation coil 400 is used to block the effect of the excitation magnetic field Bs on the cell 110 (S402).

Next, a detection step (S600) for radiating a desired light to the cell 110 and detecting a change in the susceptibility through a transmitted light. A linearly polarized light is radiated to the cell 110 from the polarized light source 310 (S602). In general, a linearly polarized light has a characteristic that a polarization angle rotation in proportion to the magnetic polarization component that is in parallel with the light advancing direction. In order to utilize this characteristic, as illustrated in FIG. 4, the linearly polarized light that is output from the polarized light source 310 is radiated in the x-axis direction of magnetic polarization of the alkaline metallic atoms. The polarization angle of the linearly polarized light radiated in the x-direction rotates in proportion to the x-axis component of magnetic polarization of the alkaline metallic atoms. The transmitted light detector 320 measures polarization angle of the transmitted light that has passed the cell 110 (S604). If the polarization angle is measured, the susceptibility detector 330 can detect the x-axis component of magnetic polarization (a component in parallel to the advancing direction of the polarized light) of the alkaline metallic atoms, using a signal of polarization angle. From a change in the detected x-axis component of magnetic polarization of the alkaline metallic atoms, a change in the susceptibility of the specimen can be detected (S606).

Thereafter, based on the change in the susceptibility of the specimen obtained in the detection step (S600), the concentration of antibodies contained in the specimen can be obtained (S700). The x-axis component of magnetic polarization of the alkaline metallic atoms varies by the antigen-antibody reaction between the antigen combined with the magnetic nanoparticles and the antibody being a bio-molecule. Thus, the concentration of antibodies, which are bio-molecules, can be measured through a reverse calculation.

The step of obtaining the concentration of bio-molecules (S700) will be explained as follows. The change in the specimen susceptibility in the detection step (S600) is normalized with the case where the specimen does not contain bio-molecules, thereby obtaining a calibration curve (S702). Based on this calibration curve, the concentration of bio-molecules can be procured in a quantitative manner, regardless of concentrations of the magnetic nanoparticles, antibodies and the like contained in the specimen unit 1000 (S704).

Using the above-described method, a detection case of Leuco Malachite Green, which is used as local antibiotics, will be described hereafter. The Leuco Malachite Green, which is used to prevent parasite insects and water molds against aquatic creatures such as fish, does not vanish in the fish flesh, but is accumulated therein. This Leuco Malachite Green is found out as a strong carcinogenic substance. It has been found out that the ultra-sensitive AC susceptibility detection apparatus of the invention can detect this substance with a sensitivity of $10^{-8}$ ppb. This means a great improvement in the measuring sensitivity, as compared with 0.12 ppb in the conventional susceptibility attenuation immuno-assay method using an induction coil, and $10^{-6}$ ppb in the conventional superconducting quantum interference device.

In another embodiment, the apparatus of the invention can be applied to precision measurement of AC susceptibility in a general magnetic material, along with the above explained biological applications such as antibodies or Leuco Malachite Green as bio-molecules. In the ultra-sensitive AC susceptibility detection apparatus of the invention, susceptibility can be measured in case of small quantity of specimen such as thin films, without necessity of reducing the temperature of the sample to an extremely low temperature. Therefore, the apparatus can be used to examine various characteristics of magnetic materials, regardless of their thickness or quantity. While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

That which is claimed is:

1. An ultra-sensitive susceptibility detection apparatus of anharmonic resonance measurement type using an atomic magnetometer, in which a change in susceptibility by a specimen containing an object to be measured is detected, the apparatus comprising:
    an atomic magnetometer including: a cell containing an alkaline metallic atom, which is affected by a magnetic field caused by the specimen; a light source for magnetically polarizing the alkaline metallic atom of the cell; and a bias magnetic field applicator for applying a bias magnetic field Bo to adjust a measuring resonance frequency of the alkaline metallic atom;
    an excitation magnetic field applicator for applying an excitation magnetic field Bs to the specimen to magnetically excite the specimen, the excitation magnetic field Bs being comprised of a plurality of AC magnetic fields $Bs_1$ and $Bs_2$ having different frequencies, respectively and, in which a direct coupling of the excitation field with the atomic resonance is eliminated by matching the atomic resonance frequency not to the individual excitation field frequencies but to a linear combination of the two frequencies; and
    a measuring device for measuring a change in magnetic polarization of the alkaline metallic atom, which is affected by a magnetic field B caused by the specimen being magnetically excited by the excitation magnetic field Bs.

2. The apparatus according to claim 1, wherein the direction of the bias magnetic field Bo is in parallel to the direction of magnetic polarization of the alkaline metallic atom.

3. The apparatus according to claim 1, wherein the excitation magnetic field Bs is perpendicular to the bias magnetic field Bo.

4. The apparatus according to claim 1, wherein the excitation magnetic field applicator is provided with a plurality of excitation coils for generating AC magnetic fields having desired frequencies, wherein the frequencies $f_1$ and $f_2$ of the respective AC magnetic fields and the integer times thereof have a value different from the measuring resonance frequency of the alkaline metallic atoms.

5. The apparatus according to claim 1, wherein the excitation magnetic field applicator further comprises an attenuation coil to reduce the direct effect of the excitation magnetic field Bs to the cell.

6. The apparatus according to claim 1, wherein a linear summation $af_1+af_2$ of the frequencies $f_1$ and $f_2$ of the AC magnetic fields is the measuring resonance frequency $\gamma Bo/2\pi$ of the alkaline metallic atoms.

7. The apparatus according to claim 1, wherein the cell is disposed inside an oven structure for shielding heat loss of the cell.

8. The apparatus according to claim 1, further comprising a vacuum tube around the cell to prevent the refractivity change of the air in the light path from heated air flow and to block heat loss from the cell.

9. The apparatus according to claim 1, wherein the measuring device includes:
    a polarized light source that radiates a polarized light to the cell;
    a transmitted light measurement and susceptibility detection portion for measuring a polarization angle of a transmitted light passing through the cell and for detecting susceptibility of the specimen based on a signal of the polarization angle.

10. The apparatus according to claim 1, wherein the bias magnetic field applicator is formed of a plurality of coils capable of generating a uniform magnetic field.

11. The apparatus according to claim 10, wherein the plurality of the coils are Helmholtz coils.

12. The apparatus according to claim 1, further comprising a magnetic field shielding device for blocking noise magnetic fields except for magnetic fields required for measurement.

13. The apparatus according to claim 1, wherein the object to be measured is bio-molecules treated with magnetic nanoparticles or a magnetic body.

14. A method of using an ultra-sensitive susceptibility detection apparatus of anharmonic resonance measurement type using an atomic magnetometer, the method comprising the steps of:
    filling a specimen in a specimen unit, the specimen containing an object to be measured;
    radiating light, from a light source, to a cell containing alkaline metallic atoms to optically pump the alkaline metallic atoms contained in the cell;
    applying a bias magnetic field Bo, from a bias magnetic field applicator, to the cell containing the optically pumped alkaline metallic atoms;
    applying an excitation magnetic field, from an excitation magnetic field applicator, to the specimen unit, the excitation magnetic field including a plurality of AC magnetic fields $Bs_1$ and $Bs_2$ having desired frequencies $f_1$ and $f_2$ to excite the specimen; and
    detecting a change in susceptibility of the specimen, with a measuring device, based on a change in magnetic polarization of the cell that is caused by a magnetic field B of the excited specimen through the excitation magnetic filed Bs.

15. The method according to claim 14, wherein in the step of optically pumping, the light is a circular polarized light.

16. The method according to claim 14, between the step of applying an excitation magnetic field and the step of detecting, further comprising a step of adjusting the bias magnetic field Bo such that a linear summation $af_1+bf_2$ of the frequencies $f_1$ and $f_2$ of the plurality of the AC magnetic fields matches the measuring resonance frequency $\gamma Bo/2\pi$ of the atomic magnetometer.

17. The method according to claim 14, wherein the step of applying the excitation magnetic field further comprises a step of attenuating the excitation magnetic field affecting the cell using an attenuation coil.

18. The method according to claim 14, wherein the step of detecting includes the steps of:
    radiating a linearly polarized light to the cell;
    measuring a polarization angle of transmitted light passing through the cell; and detecting a change in the magnetic polarization of the alkaline metallic atoms, based on a signal of the polarization angle and detecting a change in susceptibility of the specimen.

19. The method according to claim 14, further comprising a step of obtaining concentration of bio-molecules based on the change in the susceptibility of the specimen.

20. The method according to claim 19, wherein the step of obtaining the concentration of the bio-molecules includes the steps of:

normalizing the change in the specimen susceptibility obtained in the step of detecting to a susceptibility of the specimen where the specimen does not contain bio-molecules to thereby obtain a calibration curve, and obtaining a quantitative concentration of the bio-molecules using the calibration curve.

* * * * *